United States Patent
Burns et al.

(10) Patent No.: US 10,288,539 B2
(45) Date of Patent: May 14, 2019

(54) METHOD FOR TESTING OF FLEXURAL FATIGUE RESISTANCE AND ASSOCIATED SYSTEM THEREOF

(71) Applicant: General Electric Company, Schenectady, NY (US)

(72) Inventors: Andrew Arthur Paul Burns, Niskayuna, NY (US); Eugene Pauling Boden, Scotia, NY (US); Scott Michael Miller, Clifton Park, NY (US); Kathryn Amanda Misner, Duanesburg, NY (US); Terry Lee Saunders, Clifton Park, NY (US); Donald Joseph Buckley, Jr., Schenectady, NY (US)

(73) Assignee: General Electric Company, Schenectady, NY (US)

(*) Notice: Subject to any disclaimer, the term of this patent is extended or adjusted under 35 U.S.C. 154(b) by 179 days.

(21) Appl. No.: 15/230,488

(22) Filed: Aug. 8, 2016

(65) Prior Publication Data
US 2017/0108420 A1   Apr. 20, 2017

Related U.S. Application Data

(60) Provisional application No. 62/242,343, filed on Oct. 16, 2015.

(51) Int. Cl.
*G01N 3/20* (2006.01)
*G01N 3/42* (2006.01)
*G01N 3/32* (2006.01)

(52) U.S. Cl.
CPC .......... *G01N 3/42* (2013.01); *G01N 3/20* (2013.01); *G01N 3/32* (2013.01); *G01N 2203/0007* (2013.01); *G01N 2203/0073* (2013.01)

(58) Field of Classification Search
CPC ................... G01N 3/42; G01N 3/20
See application file for complete search history.

(56) References Cited

U.S. PATENT DOCUMENTS

| 8,252,397 B2 | 8/2012 | Breck |
| 2011/0151551 A1 | 6/2011 | Yi et al. |
| 2013/0125513 A1 | 5/2013 | Breck |
| 2014/0318219 A1 | 10/2014 | Hodgkinson et al. |

OTHER PUBLICATIONS

Vachette et al., "Robust and Convenient Single-Use Processing: The Superior Strength and Flexibility of Flexsafe Bags", http://www.bioprocessintl.com/manufacturing/single-use/robust-convenient-single-use-processing-superior-strength-flexibility-flexsafe-bags/, Sep. 23, 2014.

*Primary Examiner* — Paul M. West
*Assistant Examiner* — Mark A Shabman
(74) *Attorney, Agent, or Firm* — Arent Fox LLP (57) ABSTRACT

Provided herein are methods and systems for rapid testing of films used in the manufacture of bioprocess bags. The methods described herein allow for determination of resistance to flexural fatigue while mimicking actual conditions in bioprocesses such as flexion and subsequent fatigue and failure of a bioprocess bag made of a film when it is placed on a rocking platform.

16 Claims, 8 Drawing Sheets

Rocker Test

Flex Testing

METHOD FOR TESTING OF FLEXURAL FATIGUE RESISTANCE AND ASSOCIATED SYSTEM THEREOF

CROSS REFERENCE TO RELATED APPLICATIONS

This application claims the benefit of U.S. Provisional Application No. 62/242,343, titled "Flexural Fatigue Testing for Bioreactor Films", filed on Oct. 16, 2015, which is incorporated herein by reference in its entirety.

FIELD

The disclosure relates generally to an improved method for testing flexural fatigue resistance of a bioprocess film.

BACKGROUND

The fields of biopharmaceutical processing and cell therapy are adopting single-use, closed systems throughout their workflows to enhance sterility, minimize waste wash effluent and enable manufacturing flexibility compared to traditional stainless steel bioreactors. One typical single-use technology in use is a bioreactor employing rocking motion, such as a WAVE Bioreactor™. A rocking bioreactor generally comprises a bag outfitted with ports and sensors, mounted on a tray, and a control system for controlling temperature, agitation, and media perfusion. The rocking motion of the bioreactor helps in mixing the contents of the bag during cell culture.

The cell culture bags employed for use in rocking bioreactors are made by sealing flat polymer films and the bags are stored flat until use. The bags are expanded upon filling with liquid growth medium and sparging gas during cell-culture. The medium and gas filled, expanded bags, made of polymer films, often develop creases and/or dimples, which can move under rocking motion. Over a period of time, the continuous imposition of cyclic stresses due to the rocking motion of the bioreactor, possibly in combination with the volumetric strain developed due to expansion of the medium filled bags and the motion of the liquid which reverse direction during each rocking cycle can lead to flexural fatigue of the polymer film used to manufacture the bags.

In the case of small-scale cell culture, generally, the cell culture bags are filled with lower volumes of media and the bags are subjected to less extreme rocking agitation. The low volume and/or lower rate of agitation results in deformation of the cell culture bag, but the deformation does not generally lead to the flexural fatigue and/or bag failure. However, the deformation in cell culture bags employed for rocking bioreactors can lead to flexural fatigue failures when the bags are used under extreme conditions, such as use of large media volume (such as, 25 liters or more), high rates of agitation generated from rocking motion of the bioreactor and/or long culture times (tens of days) or are improperly used (e.g., mis-mounted or underinflated). Flexural fatigue can cause a range of failures (e.g., whitening, delamination or cracking, followed by leakage and/or ingress of contaminants) of the cell culture bags used in rocking bioreactors, depending on a number of factors including the material and volume of the bag, internal pressure within the bag, angle at which the bioreactor is rocking, the rate of rocking of the bioreactor, and the duration of the rocking.

Several flexural fatigue-testing systems are currently available. However, none of these systems can effectively mimic the creases and/or dimples formed on a cell culture bag used in a rocking bioreactor, the geometry surrounding the creases and/or dimples on the bag, or the other forces imposed on the medium-filled bag during cell-culture and rocking of the bioreactor. The cell culture bags or films (used for such bags) are typically tested using a "rocker test", which mimics the condition of using a rocking bioreactor on a film/bag and the test is essentially a real-time test of a film/bag used on a rocking bioreactor. However, while the rocker test can generate the dimples and/or creases on the bags, under conditions that the bags need to be used for large scale cell culture (e.g., at least 25 L scale), with continuous rocking at a high rate/angle for longer duration (e.g., more than a month), the rocker test for flexural fatigue testing is a low throughput, time consuming, labor intensive method, and it does not necessarily take films to failure (e.g., perforation or breaking) if a chosen time threshold is used.

There is thus a need for improved systems and methods, which can allow for rapid and reproducible flexural fatigue testing of the polymer film-based bags, which are typically used in bioreactors. Identification of fatigue resistant polymeric materials and/or bags made therefrom is a significant aspect of achieving robust cell cultures in bioreactor processes.

BRIEF DESCRIPTION

Provided herein are improved systems and methods for testing the flexural fatigue resistance of polymer films. The systems and methods provided herein effectively mimic the creases and/or dimples formed on a film in a bag used in a rocking bioreactor. The methods described herein allow for measurement of the flexural fatigue resistance of films in reduced time compared to the currently used methods for testing flexural fatigue resistance of films used in rocking bioreactors.

Figure 3:
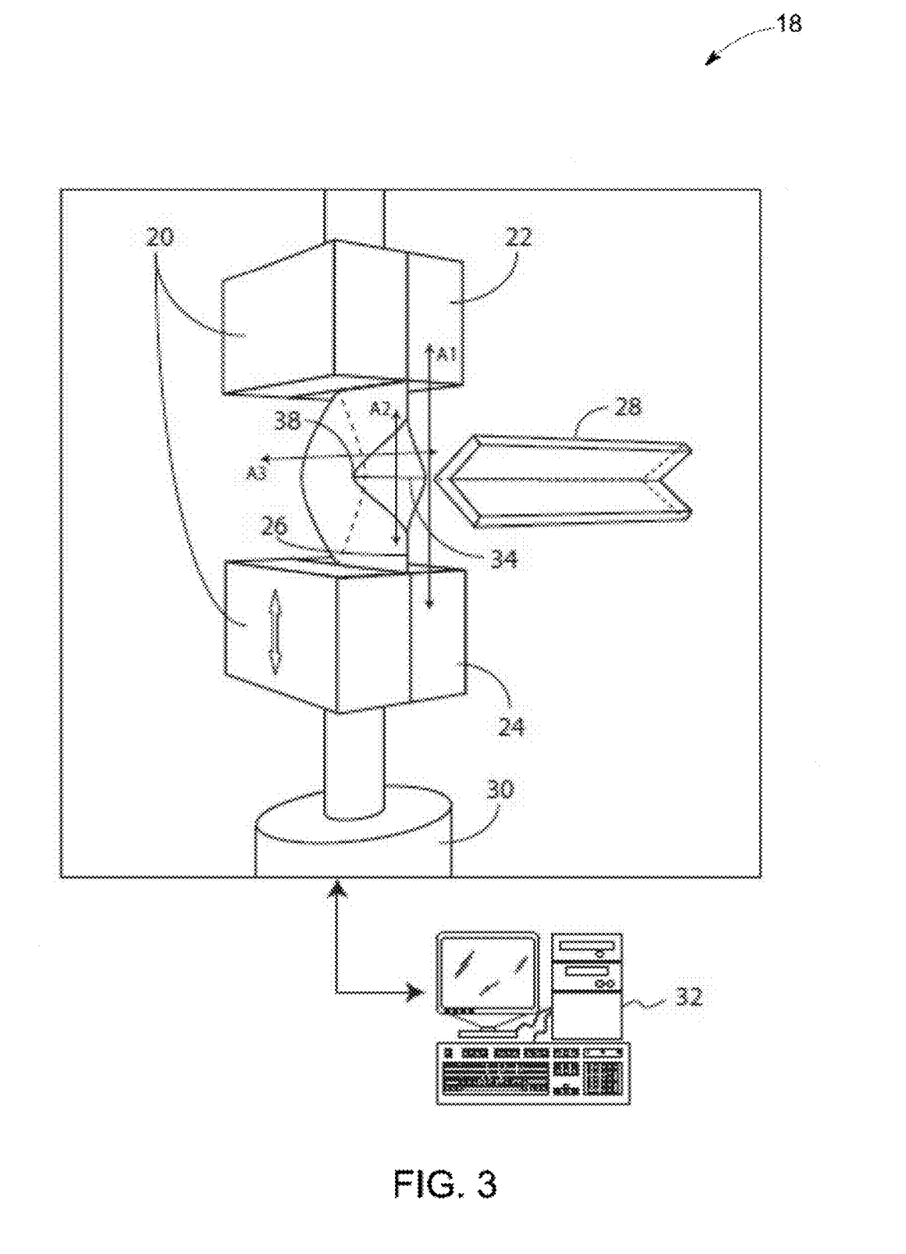
FIG. 3 is a schematic representation of a system configuration, in accordance with one embodiment of the invention.

In one embodiment, a system for testing the flexural fatigue resistance of single-layer or multi-layer polymeric films is provided, as shown in FIG. 3. The system comprises a mounting device to mount one or more film in a folded, but not creased conformation and provide a pre-load tension to the film, the mounting device comprising two film holders positioned on an axis A1 (see FIG. 3); wherein the fold in the mounted film is parallel to the axis A1, and wherein the folded film has one axis A2 parallel to the fold and a second axis A3 parallel to the film-contacting surfaces of said film holders. The system also comprises an indenter positioned between the two film holders and contacting the folded edge of the film, the indenter being angled to the axes A2 and A3, and capable of moving in a plane defined by the axes A2 and A3, to create an indentation with a depth or a radius of curvature, or a combination thereof, on the mounted film. The system also includes a device for moving at least one of the film holders at a set frequency and set amplitude for generating a reproducible displacement on the mounted film; and a recording device to record the flex fatigue resistance of the indented film to the reproducible displacement.

In another embodiment, a method for testing flexural fatigue resistance of single-layer or multi-layer films is provided. The method includes (a) introducing a fold into one or more than one film; (b) mounting the folded film such that one end of the folded film is held by a first film holder and the other end of the folded film is held by a second film holder, wherein the two film holders are positioned on an axis A1, the fold in the film is parallel to A1, the folded film has one axis A2 parallel to the fold and a second axis A3 parallel to the film-contacting surfaces of said film holders; (c) contacting the folded edge of the film with an indenter to create an indentation having a depth or a radius of curvature, or a combination thereof, on the mounted film; (d) oscillating at least one of the film holders to generate a reproducible displacement on the indented film of step [0051]; and (e) recording the flex fatigue resistance of the indented film to the reproducible displacement.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIGS. 6A-6C and FIGS. 7A-7C are comparisons of actual rocking bioreactor bags to test films. FIGS. 6A-6C illustrate the stepwise progression of failure from whitening to breaking or perforation failure in an actual 50 L rocker bag that was rocked under extreme conditions on a rocker platform.

FIGS. 7A-7C illustrate the stepwise progression of failure from whitening to breaking or perforation failure in film samples tested using methods described herein.

DETAILED DESCRIPTION

One of the challenges encountered in rocking bioreactor bags is the fact that upon inflation with air or filling with media, the originally flat bioreactor bags often develop folds and dimples during use. These deformations (e.g., folds or dimples) tend to be inconsequential at small volumes and low agitation rates or times, but can lead to flex fatigue failures such as whitening, delamination and through cracking under more extreme conditions. In practice, these failures are dependent on a number of factors including bag material and volume, mounting geometry, extent of bag inflation, rocking angle and rate, and the duration of culture, making a systematic study of the material properties controlling this behavior difficult and time-consuming.

Screening of the film materials suitable for rocking bioreactor is currently achieved by a "rocker test", wherein a large liquid volume and a long continuous run at high rock rate is required to test failure of the film material. To this end, provided herein are accelerated test methods to analyze the flexural fatigue behavior of multilayer rocking bioreactor films. The methods described herein enable quality control testing of film lots, and have the potential to compare different film compositions with a rapid and reproducible test, thereby facilitating development of new films.

The methods described herein model flexure in bags, particularly bags on rocking platforms, including the local geometry surrounding folds or dimples in a rocking bioreactor in small samples of films, and cycle the samples (at increased rates and more extreme local geometries) to accelerate flexural fatigue at the sites of the dimples or folds. In some instances, the methods described herein provide the ability to accelerate film failure from tens of days on a rocking bioreactor platform (using a medium-filled bioreactor bag) to tens of hours using less than ten square inches of a test-film.

Accordingly, in one embodiment, the present methods and systems for testing flexural fatigue failure of a film provide rapid pre-screening of the film, which helps in preliminary selection of suitable films for bags before the films/bags are subjected to the time-intensive rocker tests.

Current screening of new film materials requires rocking bioreactor testing at 50 L scale or larger, which requires multiple bioreactors to run for at least 30 days at high rate and/or angle. While this test is the most representative of the rocking bioreactor, it is susceptible to artifacts in bag mounting, it is low throughput (limited number of rocking bioreactor platforms running continuously for more than 30 days), and it does not necessarily take films to failure (breaking or perforation), only to a set threshold time (for example, 30 days). Thus, while this test is necessary as a validation of any new material, it is not suited to rapidly comparing multiple film designs or lots. The methods described herein simulate the cyclic folding seen in rocking bioreactor use, but with 1) higher cycling rate, 2) more reproducible folding (limiting asymmetry to enable more consistent results) and 3) more extreme folding geometries to push the film to fail faster. From a statistical standpoint it is advantageous to take all tests to failure, a significant attribute of this method.

Figure 1:
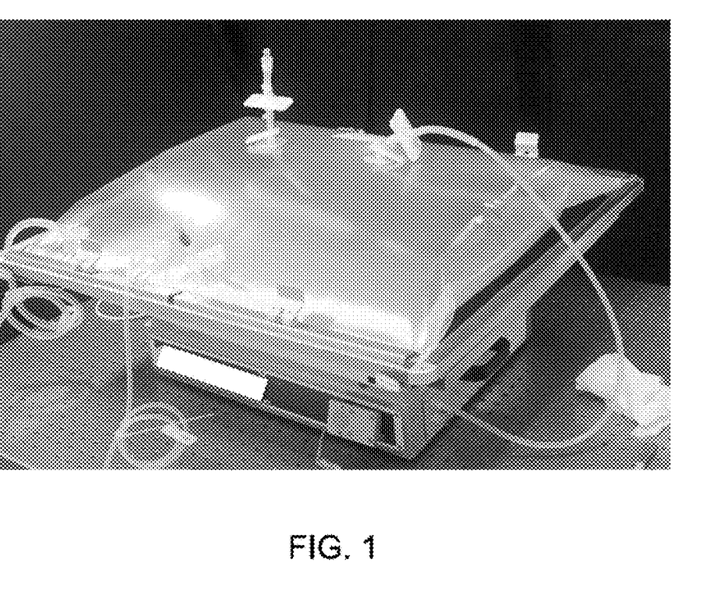
FIG. 1 shows a polymer film-based cell culture bag mounted on a rocking bioreactor platform for determining flexural fatigue of the film in a rocker test.

FIG. 1 depicts a top view of an inflated bag that resides on a rocking bioreactor, wherein one or more dimples are formed on the bag. In order to assess performance of a polymer film-based bag used in a rocking bioreactor, testing of the flexural fatigue resistance of the polymer film-based bag prior to use of the bag in the reactor is desirable. In the rocker test, dimples are introduced in a medium filled bag placed on a rocking bioreactor and the flexural fatigue resistance of the bag is recorded. In some cases, multiple cycles are required to achieve failure. The screening of polymer film-based bags using the rocker test requires the bags to be filled with at least 25 L of liquid and requires multiple bioreactors to run for a set period of days at high rocker speed/angle, such as 25 rpm at an angle of 9°. In an exemplary embodiment, a 50L rocking bioreactor (25 L effective media volume) is used in a rocking bioreactor to quantify stress on the dimple geometries under static and rocking conditions to understand the film stresses.

Figure 2A:
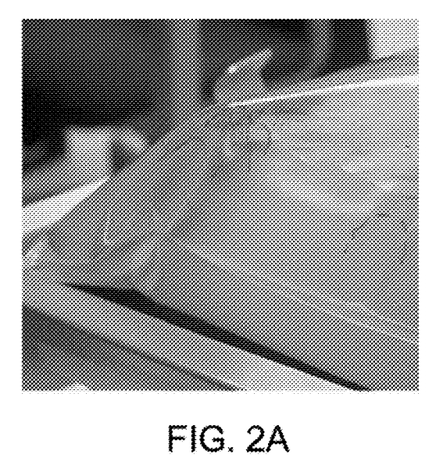
FIGS. 2A, 2B and 2C show different stages of dimple formation on a medium-filled polymer film-based cell culture bag subjected to rocking on a rocking bioreactor platform in a rocker test.
Figure 2B:
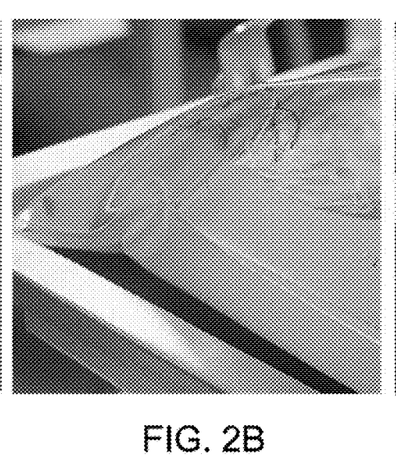
Figure 2C:
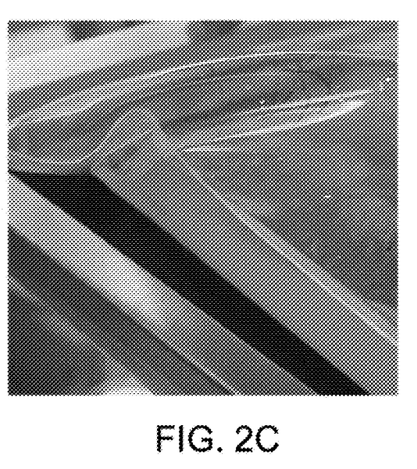

FIGS. 2A-C illustrate the folding and unfolding of the film of the medium-filled cell culture bag during the rocking motion of the bioreactor. The folding and unfolding of the film of the cell culture bag generates creases and/or dimples, which roll, pivot and elongate during rocking, generating local stresses on the film of the bag. However, this rocker test is difficult to use as a tool for screening different polymeric films, as this test is time intensive, and does not always result in failure (such as, breakage or perforation) of the test films. Thus, this test is not suitable for rapidly comparing flexural fatigue resistance of multiple films in order to select an optimal film for manufacture of bioprocess bags. The rocker test also does not allow for rapid testing of fatigue resistance of bioprocess bags made of different polymers.

In contrast, the test methods and systems provided herein are able to reproduce the local geometry around creases and/or dimples formed in/on the polymer film-based bags used in a rocking bioreactor in a small sample of film. The present methods and systems simulate the repeated flexure of a film or bag such as folding and unfolding which generates creases and/or dimples on the film by using a rocking bioreactor with higher rate of rocking. The higher rate of rocking of the bioreactor and repeated cycles of rocking ensure faster failure of the film.

In the following specification and the claims, reference will be made to a number of terms, which shall be defined to have the following meanings.

The singular forms "a", "an" and "the" include plural references unless the context clearly dictates otherwise. As used herein, the term "or" is not meant to be exclusive, and refers to at least one of the referenced components being present and includes instances in which a combination of the referenced components may be present, unless the context clearly dictates otherwise.

Approximating language, as used herein throughout the specification and claims, may be applied to modify any quantitative representation that could permissibly vary without resulting in a change in the basic function to which it is related. Accordingly, a value modified by a term or terms, such as "about", and "substantially" are not to be limited to the precise value specified. In some instances, the approximating language may correspond to the precision of an instrument for measuring the value. Here and throughout the specification and claims, range limitations include all the sub-ranges contained therein unless context or language indicates otherwise.

Figure 4A:
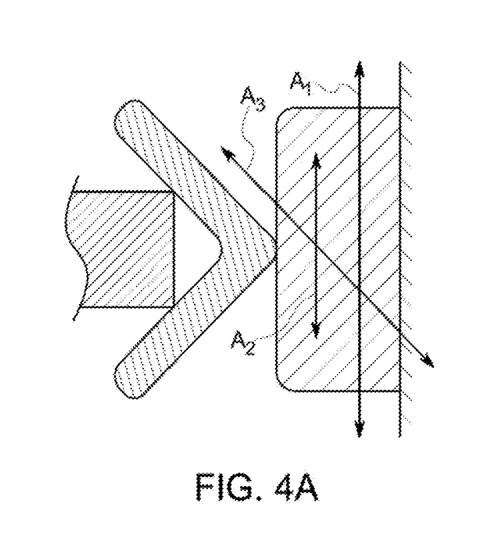
FIGS. 4A-4C depicts three different steps of a protocol for creating an indentation using an indenter on one or more films, in accordance with one embodiment of the invention.
Figure 4B:
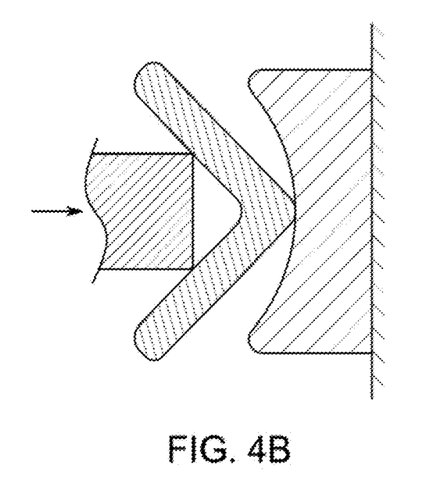
Figure 4C:
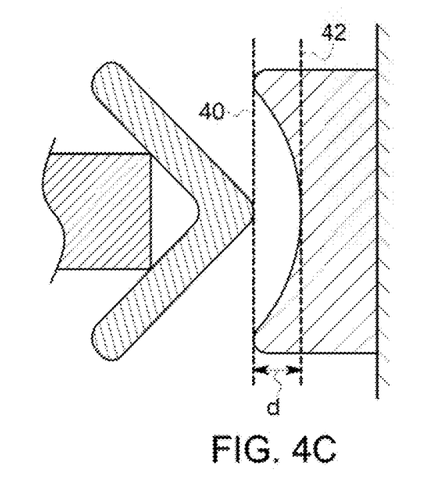

As used herein, the term "depth" refers to a distance measured from the peak of the valley formed by a dent or fold to the trough of the same valley (when viewed in cross-section). For example, as illustrated in FIG. 4 C, a depth (d) of an indentation on the film refers to the distance from the peak 42 of the indent formed to the surface 40 of the film.

As used herein, the term "radius of curvature" refers to a reciprocal of the curvature of a curve, which is a part of a circle, a cylinder, an elliptical cylinder, and the like. For a curve, the radius of curvature is equal to the radius of the circular arc which best approximates the curve at that point. For example, a radius of curvature of an indentation means the radius of curvature is equal to the radius of the curved indentation formed on the film.

The methods described herein involve folding a piece of the desired film to be tested in half prior to inserting into the mounting device, and optionally thermally sealing one, two or all three of the remaining sides. For the purposes of this invention, a "folded" film is differentiated from a "creased" film, wherein a creased film remains in the creased configuration without any mechanical stimulus, while a folded film tends to unfold and become flat if not mechanically held in the folded conformation. Opened or closed, this test sample is referred to as a "bag". In one embodiment, the open or closed bags can be a variety of sizes, e.g., range in size from 2.5 cm×5 cm to about 20 cm×50 cm. The bag is then mounted into an instrument that is capable of generating a reproducible stress on the sample along the long axis of the film. FIG. 3 shows a schematic of this device, including the axis A1 along which the repetitive motion is applied, and the parallel axis A2 which represents the longest axis of the film. In certain embodiments, one side of the bag is held in a fixed position, which does not move during the test. In these embodiments, the other side of the bag is securely held by a holder, wherein the holder may be oscillated in the direction of axis A1 in a controlled manner. The initial position is to have the film mounted such that it is substantially elongated with little or no load on the film. Optionally, to aid alignment, the film can be clamped in a vertical position (i.e., axis A1 vertical) with the first holder securing the film at the top. A weight may then be attached to the bottom to cause the film to hang vertically and the bottom clamp may be secured to the film and the weight removed.

In one aspect, provided herein is a system to measure flex fatigue resistance in multilayer bioprocess films comprising: a mounting device to grip film and provide preload pressure having a fixed grip and a mobile grip; an indenter to create a specific depth and radius of curvature to be tested; a device for moving the mobile grip at a set frequency and amplitude and a recording device to measure response of the film to the induced flexing.

The system comprises a mounting device comprising two film holders, an indenter, a device for moving at least one of the film holders; and a recording device. The mounting device is employed to mount one or more than one film in a folded conformation. In some embodiments, a pre-load tension is provided to the film. The mounting device comprises two film holders positioned on an axis A1 (FIG. 3); wherein the fold in the mounted film is parallel to the axis A1, and the folded film has one axis A2 parallel to the fold and a second axis A3 parallel to the faces of said film holders. The device for moving at least one of the film holders is employed to move at least one of the holders at a set frequency and set amplitude for generating a reproducible displacement on the mounted film at least substantially along axis A1. During the initial cycling of the device, the indenter is positioned between the two film holders and contacting the folded edge of the film, the indenter being angled to the axes A2 and A3, and capable of moving in a plane defined by the axes A2 and A3, to create an indentation with a depth or a radius of curvature, or a combination thereof, on the mounted film. Once the desired indentation is established in the film, the indenter is removed. The recording device of the system is employed to record the flexural fatigue resistance of the indented film to the reproducible displacement caused by the motion of at least one of the film holders at least substantially along axis A1. The reproducible displacement refers to a shift or movement of an edge of a film from its initial position by repeated movement of the film holder(s). At least one of the film holders moves at a set frequency and set amplitude at least substantially along axis A1, where axis A1 may be aligned vertically, horizontally or at an arbitrary angle, for generating the reproducible displacement on the mounted film.

Figure 8:
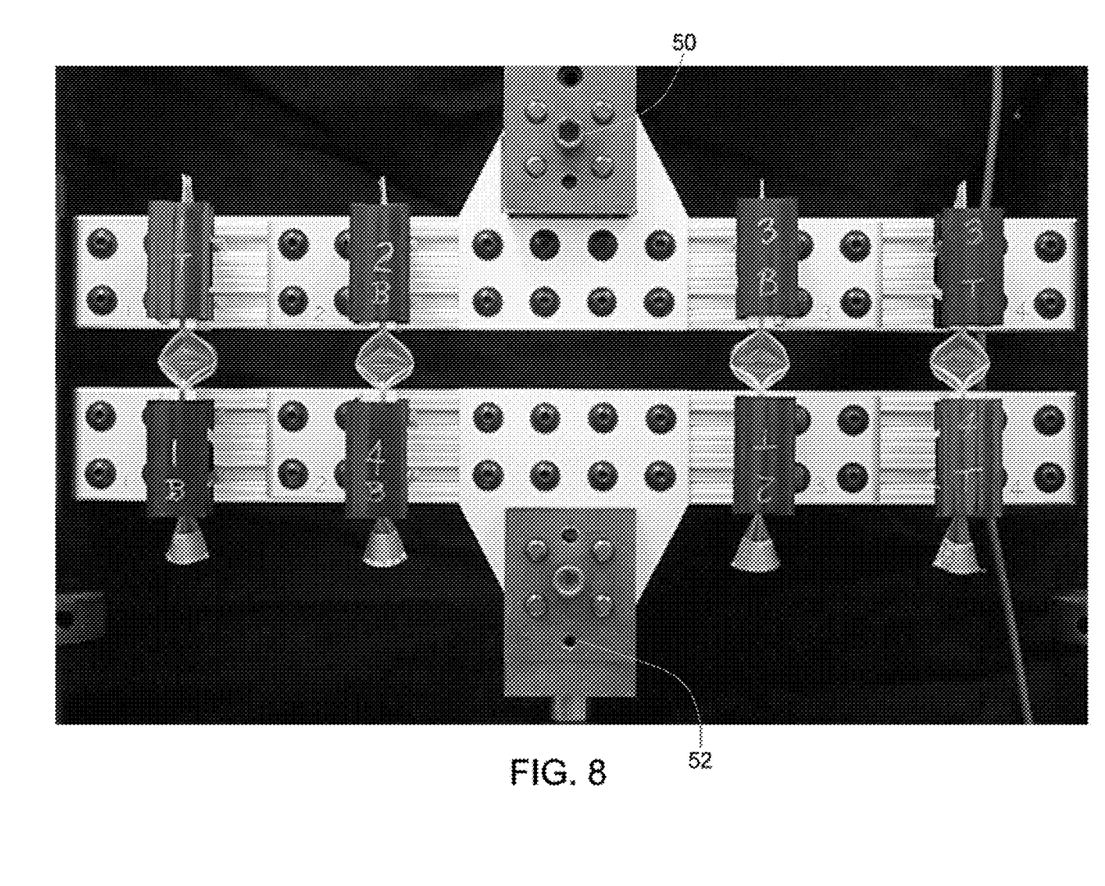
FIG. 8 is a front view of a system configuration for simultaneous testing of multiple films, in accordance with one embodiment of the invention.

A mounting device is employed to mount one or more films for testing flexural fatigue resistance of the film. The mounting device may include two or more film holders for holding one or more films during mounting. In some embodiments, the mounting device comprises two film holders, wherein the holders are coupled to a frame, which is attached to the base of the mounting device. In some other embodiments, one film holder is coupled to the top portion of the mounting device and another film holder is coupled to the base of the mounting device. The film holders are placed along an axis, separated by a distance. The distance between two film holders may be adjusted according to the length of the film used for testing flexural fatigue resistance. In some embodiments, the folded film is mounted into the mounting device, which is capable of generating a reproducible linear or cyclic displacement (and thus stress) in the film along the long axis of the film, such as the axis A2. The film holders may include, but are not limited to, a clamp, a clip, a fastener, and an adhesive. In one embodiment, the mounting device comprises two film holders for mounting a film. For example, the mounting device 20 of FIG. 3 comprises a first film holder 22 and a second film holder 24. The first film holder and the second film holder of the mounting device are positioned on an axis A1, a distance apart from each other. The distance between the two holders may be varied depending on the length of the film that needs to be mounted on the mounting device. In some other embodiments, the mounting device comprises more than two film holders to hold multiple films. For example, as shown in FIG. 8, the mounting device has eight film holders for mounting four films. In this mounting device, each of the films is mounted with the aid of two film holders, which are positioned on an axis, a distance apart from each other. The holders in the mounting device are positioned such that the films are mounted on the device in a parallel arrangement (FIG. 8).

An indentation is made by putting pressure on the center of the film on one side using an indentation device (indenter). In some embodiments, the indenter is an angle iron but can be anything having a variety of angles or even cylindrical instruments like tubing or wire. For any of the indenters, the radius of curvature can be varied in order to produce a desired difference in the indentation on the film. The depth of the indentation can be varied in order to test a variety of film types. The device is then removed and an oscillation (e.g., with a sinusoidal waveform) of the film holders is performed at low frequency to ensure that the indentation remains in a fixed position in the film. If asymmetries occur with the indentation, then this procedure can be repeated to get the desired reproducible indent. Once the indent is shown to be stable after multiple cycles, the oscillation frequency can be increased e.g., to 0.1 to 100 Hz. As the cycling proceeds, the fatiguing portion of the dimple/fold ultimately progresses through a variety of failure modes that typically show whitening, cracking and eventually complete through-hole failure. Typically, breaking or perforation failures are detected after periodically stopping the cycling using solutions of dye that are blotted on the inside of the bag at the one or both of the apices of the indentation (e.g., 38 in FIG. 3) while testing the outside of the film for penetration of the dye solution (e.g., with an absorbent material). Other methods of detection including taking video of the process and various optical means of using white light or low powered lasers in combination with various means of detection, including light meters and polarization techniques.

A fully sealed bag on all sides affords additional ways to the test for failures. In this case, the indentations can be formed on both the front and back sides of the bag (i.e., generating two indentations, and four apices instead of one indentation and two apices as above). This not only provides more potential failure points but also affords the opportunity to pressurize the bag with air or introduce dye-colored or conductive aqueous solutions into the bag. Additional failure modes could then include hydrostatic pressure introduced by the aqueous solution and may simulate better the failure mode in an actual rocking bioreactor bag. There are also variations on indentation that can simulate various failure modes. For example, the two fold points produced by the indentation device do not need to be symmetrical and could potentially even be a single fold. This could in part change the amount of stress at the fold and help to accelerate the testing and/or effect reproducibility.

In some embodiments, the indenter is attached to a stand. Both ends of the stand are coupled to the sliding channels present on the top portion and the bottom portion of the present system. The indenter is positioned between the two film holders such that the indenter is able to slide forward to contact the film. In these embodiments, the indenter is able to slide along the surface of the plane that is perpendicular to the folded edge of the film (the plane defined by axes A2 and A3 in FIG. 3). In some embodiments, the indenter is mounted such that the indenter can move along the surface of the plane that is perpendicular to the folded edge of the film without changing the orientation of the indenter. In some embodiments, the sliding movement of the indenter may be controlled manually or by using a computer based program. In these embodiments, the system is coupled to a computer. The computerized program may be pre-set such that the indenter slides through the plane that is perpendicular to the mounted film and contacts the film in response to a command sent from the computer. The repetitive movement of the indenter may also be controlled by setting a computerized program. The oscillation of the holders may also be regulated by a computer. A pre-set computer based program generates different commands to control the frequency of the oscillation.

In some embodiments of the system, the indenter is an angle-iron. Generally, an angle iron is an angular metal piece, formed when a metal bar is bent at an angle along its longest dimension. In one or more embodiments, the indenter is a rigid cylinder, elliptic cylinder, hemicylinder or hemi-elliptic cylinder having a diameter or long axis length ranging from about 0.5 mm to about 20 mm. An angle of the angle-iron may be varied in a wide range, such as an angle from about 10° to about 170°.

In one or more embodiments, the indenter is an angle-iron comprising an angle ranging from about 10° to about 170°. In some embodiments, the angle-iron has an angle in a range from about 30° to about 150°. In some other embodiments, the angle-iron has an angle in a range from about 50° to about 120°. In one or more embodiments, the angle-iron has an angle in a range from about 70° to about 100°. In one embodiment, the angle-iron has an angle of 90°.

In a group of embodiments, an indenter has a profile comprising an elliptical curve or an arc and has a radius of curvature. The radius of curvature of any indenter may be varied in order to produce a desired indentation on a film. In some embodiments, an indenter has a radius of curvature ranging from about 0.1 mm to about 10 mm. In some other embodiments, the radius of curvature of the indenter may be in a range from about 0.5 mm to about 8 mm. In some embodiments, the radius of curvature of the indenter may be in a range from about 1 mm to about 5 mm.

In one or more embodiments, the indenter is a rigid cylinder or hemicylinder having a diameter ranging from about 0.5 mm to about 20 mm. In some embodiments, a diameter of the indenter is in a range from about 1 mm to about 15 mm. In some other embodiments, the indenter has a diameter in a range from about 5 mm to about 10 mm.

A recording device is employed to record the flexural fatigue resistance of the indented film, wherein the recording device may include a camera, a photodetector and/or a computer. The camera may be used for capturing images of different steps of the progression of failure of the film, such as whitening, delamination, perforation, or breakage of the film. A computer may be used to record the level of stress applied to the film and the time required for the failure, such as the time required for the film to become perforated. Embodiments of the structure of the flexural fatigue testing system are described in greater detail hereinafter, and further illustrated in FIGS. 3, 4A-C, 5A, 5B, and 8.

FIG. 3 illustrates some embodiments of the system; wherein the system 18 comprises a mounting device 20. The mounting device comprises two film holders, such as a first film holder 22 and a second film holder 24. The first film holder 22 and the second film holder 24 are positioned on an axis A1, a distance apart from each other. The distance between the two holders may be varied depending on the length of the film that needs to be mounted on the system.

In some embodiments, the distance between the two film holders may be in a range from about 1 cm to about 100 cm. In some other embodiments, the distance between the two film holders may be in a range from about 2 cm to about 50 cm. In another embodiment, the distance between the two film holders is in a range from about 3 cm to about 6 cm. In one example embodiment, the distance between the two film holders may be about 4 cm.

The film to be tested for flexural fatigue resistance is mounted in the mounting device of the system in a folded conformation. The fold in the mounted film 26 (FIG. 3) is parallel to the axis A1, wherein the folded film has one axis A2 parallel to the fold and a second axis A3 parallel to the faces of said film holders 22 and 24. The system 18 also comprises an indenter 28, positioned between the two film holders 22 and 24.

Figure 5A:
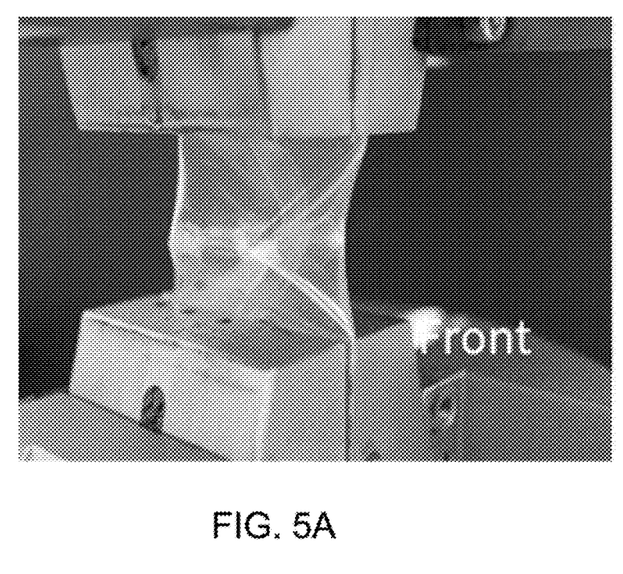
FIG. 5A depicts an image of an indentation formed on the front side of a bag mounted on a mounting device, in accordance with one embodiment of the invention.
Figure 5B:
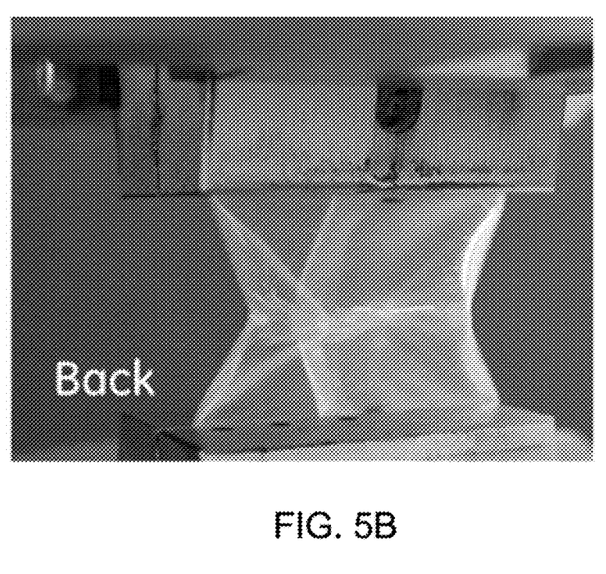
FIG. 5B depicts an image of an indentation formed on the backside of a bag mounted on a mounting device, in accordance with one embodiment of the invention.

The indenter 28 (FIG. 3) contacts the folded edge of the film 26. The indenter 28 may be an angle-iron, which has an angle in a range from about 10° to about 170°. The indenter 28 is angled to the axes A2 and A3, and capable of moving in a plane defined by the axes A2 and A3 (FIG. 3). The indenter creates an indentation on the mounted film, wherein the indenter positions during the process of indentation are illustrated in FIGS. 4A, 4B and 4C. FIGS. 4A-C depicts three different steps of indentation; first, contacting the indenter to a mounted film, second, forming an indentation by applying a minimal pressure to the film by the indenter while moving the indenter through a path in the plane defined by axes A2 and A3 as the film sample is compressed, and third, moving the indenter away from the film after forming the indentation on the film. A device 30 (FIG. 3) is employed for moving at least one of the film holders at a set frequency and set amplitude for generating a reproducible displacement on the mounted film. In addition, the recording device 32 of the system records the flexural fatigue resistance of the indented film to the reproducible displacement. FIGS. 5A and 5B further illustrate front view and back view, respectively, of a film mounted through two holders for an embodiment with double indentation (front and back).

The system provided herein may also be used for testing flexural fatigue resistance of multiple films. In one embodiment, the system allows for the testing of four films simultaneously, as illustrated in FIG. 8. In FIGS. 8, 50 and 52 are the fixed and movable holders of the system, respectively. The system may be expanded to test more than one films by adding the required number of holders for holding multiple films and other required devices to run the system. In one embodiment of the system, four individually folded films may be attached to the top row of small holders (FIG. 8). Weights may be attached to the films below the holders at the bottom of the film, while these holders are open, followed by clamping. An indenter, such as an angle iron may then be pressed against the films while the holders are slowly moving to form an indent on the film.

In one or more embodiments, provided herein is a method for testing flexural fatigue resistance of single-layer or multi-layer films. The method comprises (a) introducing a fold into one or more than one film; (b) mounting the folded film such that one end of the folded film is held by a first film holder and the other end of the folded film is held by a second film holder, wherein the two film holders are positioned on an axis A1. The fold in the film is parallel to A1, the folded film has one axis A2 parallel to the fold and a second axis A3 parallel to the faces of said film holders. After mounting the folded film in step (b), the method comprises (c) contacting the folded edge of the film with an indenter to create an indentation having a depth or a radius of curvature, or a combination thereof, on the mounted film. The indentation on the mounted film in step (c) is followed by step (d) oscillating at least one of the film holders to generate a reproducible displacement on the indented film; and (e) recording the flexural fatigue resistance of the indented film to the reproducible displacement.

The method involves a step (a) of introducing a fold into one or more than one film, wherein the film may be folded in different portions of the film. The film is folded without creasing or pinching the fold, wherein the sealed end is at the top. In some embodiments, the fold that is introduced into one or more of the films may be a linear fold. In some other embodiments, the fold that is introduced into one or more of the films may be a non-linear fold. In one embodiment, the desired film to be tested may be folded in half prior to inserting into the mounting device. In some embodiments, the film may be thermally sealed at one end, two ends or all three ends.

In some embodiments, the film is folded and sealed to mimic the structure of a bag that is used in a bioreactor. The folded film with one end open or two ends open, or the folded film with three ends closed, may be designated as a "bag". When the ends are open, it may be in a shape of an "open bag". When the three ends are closed, it may be in a shape of a "closed bag". In some embodiments, the film is part of a bioprocess bag. In some of such embodiments, the bioprocess bag is used in a bioreactor for cell culture, wherein the bioprocess bag is placed on a rocking platform of the bioreactor.

The folded film with sealed or open ends may be of a variety of sizes. In some embodiments, the size of the folded film is in a range from about 2.5 cm×5 cm to about 20 cm×50 cm. In some embodiments, the size of the folded film is in a range from about 5 cm×10 cm to about 20 cm×50 cm. In some embodiments, the size of the folded film is in a range from about 7.5 cm×15 cm to about 20 cm×50 cm.

In some other embodiments, the mounted film is further stretched by adding a load on the film. The film may be mounted in a substantially stretched form with the addition of a minimal load. The mounted film may further be stretched by attaching additional loads on the film. In some embodiments, the film may be mounted in a vertical position with the first holder securing the film at the top, a load is attached to the bottom of the film to cause the film to hang vertically and stretched to the desired extent. The second holder at the bottom then holds the stretched film, and the load is removed.

In some embodiments, an indenter contacts the folded edge of the mounted film and creates an indentation on the film. In some embodiments, the indenter is angled to the axes A2 and A3 and is capable of moving in a plane defined by the axes A2 and A3. In some embodiments, the indentation is formed by contacting the indenter with the mounted film at an angle ranging from about 0° to about 90° from the axis A2. In one embodiment, the indenter is perpendicular to the axes A2 and parallel to the axis A3. FIGS. 4A-C show a 90° angle iron, which is used to form an indent on a mounted film. Various forms of indentations include, but are not limited to, angular, oblong, half-cylinder, and elliptical cross-sections.

In some embodiments, the method further comprises moving the indenter in a direction that is perpendicular to the axis A2 and parallel to the axis A3. In these embodiments, the direction of movement of the indenter is in an angle ranging from about 10° to about 90° to the axis A2 and parallel to the axis A3. In some other embodiments, the indenter is moving in an angle ranging from about 30° to about 90° to the axis A2 and parallel to the axis A3. In some other embodiments, the indenter is moving in an angle ranging from about 60° to about 90° to the axis A2 and parallel to the axis A3.

The movement of the indenter to form an indentation is illustrated in FIGS. 4A-C. In one embodiment, the method comprises moving the indenter in a direction that is perpendicular to the axis A2 and parallel to the axis A3 of the film. This results in symmetric indentations with respect to the fold. The symmetric indentations are generally more reproducible than asymmetric ones formed without an indenter. In some other embodiments, the indenter is moving in a direction that is parallel to the axis A3 and may deviate slightly from perpendicular to the axis A2, depending on whether both of the two film holders are moving or only one film holder is moving. As noted, the indenter movement may be controlled manually or by using a computerized program. A pre-set program in a computer may run for sliding the indenter through the plane that is perpendicular to the mounted film to contact the film edge. The repetitive movement of the indenter may also be controlled by a computerized program. The movement of the film holders may also be controlled by a computer. The holders are oscillated by using a different program run by the computer. In these embodiments, the reduced repetitive movement of the indenter may accelerate the testing process. In embodiments where only one film holder moves, the midpoint between the film holders which is the position of the desired crease or dimple may also move. The movement of the position for the desired crease formation on the film may be compensated by the motion of the indenter. In some other embodiments, an indentation is formed by putting pressure on the center of the film. The indenter may be pushed into the film gently, when the distance between the two film holders is decreased and produces a crease on the film. In embodiments, where the indenter is an angle iron, the indenter is placed on the folded film such that a plane that is perpendicular to the folded edge of the film should bisect the 90° angle of the angle-iron. The angle iron may be mounted on a sliding stage so that it is able to move along the surface of the plane that is perpendicular to the folded edge of the film without changing the orientation of its 90° angle. The formation of crease on the mounted film in the system is shown in FIGS. 4A-C, 5A and 5B.

The indentation formed on the mounted film has a depth or a radius of curvature, or a combination thereof. Since different films have different capacity to withstand stress to form a desired indentation, applying the same stress on different types of films results in different types of indentations. The shape and/or depth of the indentation on different films may be different. In some embodiments, the depth of the indentation formed on the film ranges from about 5 mm to about 500 mm. In some other embodiments, the depth of the indentation formed on the film ranges from about 10 mm to about 100 mm. In some other embodiments, the depth of the indentation formed on the film ranges from about 10 mm to about 50 mm. In some other embodiments, the depth of the indentation formed on the film ranges from about 10 mm to about 30 mm.

The radius of curvature of the indentation formed on the film may be in a range from about 0.01 mm to about 10 mm. In some embodiments, the radius of curvature of the indentation formed on the film may be in a range from about 0.1 mm to about 2 mm. In some other embodiments, the radius of curvature of the indentation formed on the film may be in a range from about 0.5 mm to about 1.5 mm. In some other embodiments, the radius of curvature of the indentation formed on the film may be in a range from about 0.8 mm to about 2 mm. In some other embodiments, the radius of curvature of the indentation formed on the film may be in a range from about 1 mm to about 2 mm.

The formation of an indentation on the mounted film is followed by oscillating at least one of the film holders to generate a reproducible displacement on the indented film. The indenter is then removed and a sinusoidal oscillation of at least one of the holders is done at low frequency to further cycle the indentation and mimic the conditions (e.g., rocking platform oscillations) under which the film and/or bag comprising the film will be used. The step of oscillating at least one of the film holders may be repeated for multiple cycles. The oscillation may be regulated by a computerized program generated from a computer coupled to the system.

In some embodiments, the step of oscillating at least one of the film holders is repeated for 2 to 50 cycles to ensure stability of the indentation. The stability of the indentation refers to herein that the location of the indentation, crease, fold, or dimple does not change through the course of the flexural fatigue testing. In some other embodiments, the step of oscillating at least one of the film holders is repeated for 4 to 20 cycles to stabilize the indentation. In some other embodiments, the step of oscillating at least one of the film holders is repeated for 6 to 10 cycles to stabilize the indentation. In some embodiments, the step of oscillating at least one of the film holders is repeated for 4 to 8 cycles to stabilize the indentation.

In some embodiments, one end of the film is held in a fixed position by the first film holder and does not move during the flexural fatigue testing while the other end of the film is securely held by the second film holder that can oscillate along axis A1 in a controlled manner. If asymmetries occur with the indentation, then the method may be repeated to get the desired reproducible indentation in the film. Once the indentation is stable after multiple cycles of oscillation, the frequency of the oscillation may be increased up to about 100 Hz.

The reproducible displacement in the indented film may be produced at least substantially along the axis A1 (FIG. 3). In some embodiments, the reproducible displacement comprises a cyclic displacement, a linear displacement, a sinusoidal displacement, or combinations thereof. In some embodiments, at least one of the film holders is cycled along the axis A1 with a sinusoidal waveform. In some embodiments, the method further comprises oscillating both of the film holders to generate the reproducible displacement on the indented film.

In some embodiments, at least one of the film holders is cycled along the axis A1 in a sinusoidal wave form with a frequency ranging from about 0.01 Hz to about 100 Hz and a displacement ranging from about 10 mm to about 100 mm Once the indentation is stable after multiple cycles of oscillation, the frequency of the oscillation of at least one of the holders, such as a second holder may be increased from about 0.1 to about 100 Hz. In some embodiments, the frequency of oscillation may be in a range from about 1 to about 100 Hz. In some other embodiments, the frequency of oscillation may be increased from about 1 to about 30 Hz. In some other embodiments, the frequency of oscillation may be in a range from about 1 to about 10 Hz.

In some embodiments, at least one of the film holders is cycled along the axis A1 in a sinusoidal wave form to generate a displacement ranging from about 10 mm to about 100 mm. In some embodiments, the displacement may be in a range from about 10 mm to 50 mm. In some other embodiments, the displacement may be in a range from about 10 mm to 30 mm. In some other embodiments, the displacement may be in a range from about 15 mm to 30 mm.

In some embodiments, the oscillation of at least one of the film holders is followed by recording the flexural fatigue resistance of the indented film to the reproducible displacement. The recording of flexural fatigue resistance of a film includes detection of the failure of the film and then recording the time required for generating perforation on the film or breakage of the film. In some embodiments, the failure of the film is detected by visual inspection, cross-sectional transmission or reflectance microscopy, planar transmission microscopy, polarized light microscopy, resistance measurement, laser photodetection, continuous photodetection, dye penetration, or combinations thereof. In one embodiment, the failure of the film is detected by dye penetration. In a method of dye penetration, a solution of 0.1 to 5% by weight of Allure Red AC dye in a 50% volume of ethanol in water may be utilized. The perforation of the film may be detected using a dye solution that is blotted on the film, which penetrates through the perforations and can be easily detected on the opposite side.

In some embodiments, the flexural fatigue resistance may be recorded intermittently. The degree of fatigue of the film may be recorded by an intermittent photographing mode using an image photographing device. The photographing timing may be synchronized with the stress applied to the film using a computer. In some embodiments, the flexural fatigue resistance may be recorded continuously. In this embodiment, the fatigue condition may be captured in a real-time video during the flex fatigue testing.

In some embodiments, step (d) of the present method, i.e., the oscillation of at least one of the film holders and step (e) of the present method, i.e., recording of the flexural fatigue resistance of the indented film to the reproducible displacement are repeated until the failure of the film is observed. In some embodiments, step (d) of the present method, i.e., the oscillation of at least one of the film holders and step (e) of the present method, i.e., the recording of the flexural fatigue resistance of the indented film to the reproducible displacement are repeated for 1 to 5,000,000 cycles to measure the flexural durability of the film. In some other embodiments, step (d), i.e., oscillation of at least one of the film holders and step (e), i.e., recording of the flexural fatigue resistance of the indented film are repeated for 10 to 500,000 cycles to measure the flexural durability of the film. In some other embodiments, step (d) of the present method, i.e., oscillation of at least one of the film holders and step (e) of the present method, i.e., recording of the flexural fatigue resistance of the indented film are repeated for 100 to 50000 cycles to measure the flexural durability of the film. In some other embodiments, step (d) of the present method i.e., oscillation of at least one of the film holders and step (e) of the present method, i.e., recording of the flexural fatigue resistance of the indented film are repeated for 1000 to 20000 cycles to measure the flexural durability of the film.

In some embodiments, the oscillation of at least one of the film holders (step d) results in a failure of the film. One or more dimples may be formed on the film at the apices of the indentation (e.g., 38 in FIG. 3) due to indentation and repeated oscillation. Additionally, one or more crease may form along the line connecting the two apices of the indentation (e.g., 34 in FIG. 3). As noted, at least one of the film holders is cycled along the axis A1 in a sinusoidal wave form, wherein the repeated cycling develops flexural fatigue in the film. The fatigue weakens at least some portions of the dimple or crease, which proceeds through a variety of failure modes. The failure of the film may comprise whitening of the film, cracking of the film, delamination of the film, perforation of the film, breaking of the film, or combinations thereof. The portion of the film (see 34 and 38 of FIG. 3) which is affected most and goes through a failure mode is illustrated in FIG. 3.

In some embodiments, a folded film, sealed on three sides affords additional ways to test for flexural fatigue failure of the film/bag. In these embodiments, the indentation may be formed at the front side of the folded film, as depicted in FIG. 5A. The indentation may also be formed at the back side of the folded film, as depicted in FIG. 5B. The structure of a fully sealed folded film provides more potential failure points compared to an open ended folded film. The fully sealed folded film may be pressurized by introducing air. In some embodiments, the fully sealed folded film may be pressurized by introducing aqueous solutions. In these embodiments, the failure mode includes hydrostatic pressure introduced by the aqueous solution and may simulate better the failure mode as occurs in an actual cell culture bag used in a rocking bioreactor. During detection of failure modes, the colored dye solution may also be introduced into the fully sealed folded film to enable easy detection of failure of the film.

In the embodiments where a three sides-sealed folded film is used, the sealed and folded film reproduces the structure of a bag used for culturing cells in a bioreactor. The folded film with sealed edges used for testing flexural fatigue resistance may have a volume in a range from about 10 mL to about 1 liter. In some embodiments, the folded film with sealed edges used for testing flexural fatigue resistance may have a volume in a range from about 20 mL to about 500 mL. In some other embodiments, the folded film with sealed edges used for testing flexural fatigue resistance may have a volume in a range from about 20 mL to about 100 mL.

The present method and system for testing flexural fatigue resistance of a film may be used to differentiate performance of various polymer films in order to develop the most robust design for single use disposable (SUD) bioprocessing applications. Since the systems and methods described herein allow for rapid testing, these systems and the methods can be used for preliminary selection of the films in a short time before testing the films by rocker test using rocking bioreactors. Multilayered films, typically containing 3 to 13 layers, are commonly used in bio-pharmaceutical processing and food packaging applications. The film samples which are tested using the present method may be made of a variety of polymers which may include different types of linear polyolefin, branched polyolefin, cyclic polyolefin, or combinations thereof. In some embodiments, the polymers used for the film may include, but are not limited to, ethylene vinylacetate (EVA), ethylene vinylalcohol (EVOH), polyamides, polyimides, polyesters, fluoropolymers, polyolefins, polyesters, polyolefin ketones, polyester elastomers, thermoplastic polyurethanes, polyacrylates, copolymers, ionomers, electrically conductive polymers, or electrically insulative polymers. In some embodiments, the multilayer films used for SUD applications comprise combinations of various polymers and tie layers. The "tie layers" are generally used to bond materials with dissimilar polymer structures that are often functionalized versions of the polymers to be bonded. The testing of all such films, packaging materials, and/or cell culture bags is contemplated within the scope of embodiments described herein.

EXAMPLES

Example 1

Flexural Fatigue Testing of a Single Film

Sample preparation: Each test sample of the films used for flexural fatigue testing was cut into 3.75 cm×17.5 cm pieces. The inside surface of a bioprocess bag was made from this film, such that the cells were in a contact with the film. The film was folded in half along the longest axis of the film, such that the cell contact layer was on the interior of the fold. One of the sides of the folded film was then heat sealed to close one end of the film using an impulse heat sealer at a setting appropriate for the material. The sealed end was referred to as the 'top end' and the opposite open end of the sample film was referred to as the 'bottom end.' The film was thereafter held in its folded conformation, but not creased along the folded side. The folded film was then marked to ensure proper positioning of the film in the system. The markings were ¼" lines perpendicular to the folded edge, made using a permanent marker, midway between the folded edge and the open (not folded) edge. In the folded film (without having any crease), the markings were made at 1.25 cm, 6.25 cm, 7.5 cm, 8.75 cm, 10 cm, and 15 cm distance from top to bottom. A strip of self-adhesive material, e.g., a duct tape of 1.87 cm×3.75 cm was placed on the outer surface of the folded film along its bottom edge to increase the surface friction for clamping a weight to the film.

Mounting the sample film: The two film holders, the first holder at the upper end and the second holder at the lower end of the folded film were placed such that they were aligned vertically, with a 3.8 cm distance between the closest edges of the two holders and such that the clamps comprising the holders were parallel. The film was folded without creasing or pinching the fold, wherein the sealed end was at the top. The holders were opened and the folded film was then slid into the upper and lower holders simultaneously, with 1.3 cm of the sealed end protruding up from the first holder, and 3.8 cm of the open end protruding down from the second holder. The folded film was aligned such that the folded edge aligned vertically with the first (top) and the second (bottom) holders. The first holder was then closed around the film.

A load of 2 lb was attached to the bottom (unsealed) edge of the film below the second holder over the duct-tape covered area of the film. The second holder at the bottom of the film was then closed around the film and the 2 lb load was removed.

Indentation: A metal angle-iron, with a radius of curvature of approximately 1.5 mm, was used to indent the film. The angle iron was positioned at the midpoint of the 3.8 cm gap between the top holder and bottom holder, so that the long edge is perpendicular to the folded edge of the film. The angle iron was mounted on a sliding stage so that it was able to move along that surface that is perpendicular to A2 without changing the orientation of its 90° angle.

Indent Formation: To form the indentation on the folded film, a 90° angle iron was slid forward to contact the film. While the holder separation was decreased by manual control, the angle iron was slid forward to remain in contact with the film. When the angle-iron touched the top and bottom holders, it could no longer be kept in contact with the film during further indenting. At that point, the separation distance between the top holder and bottom holder was slowly returned to their original separation distance of 3.8 cm, and the angle iron was withdrawn to its original position, in continuous contact with the film. The indent formation process was repeated for two more times, with the angle-iron sliding to stay in continuous contact with the film.

Oscillation of the holders: The angle iron was removed and the holder separation was placed under computer control. A program of 0.1 Hz sinusoidal oscillation in holder separation between $d_1$ and $d_2$ for 30 cycles was run and monitored to verify that the indented deformation was successful. In sinusoidal oscillation, $d_1$ is maximum distance between the first holder at the top and the second holder at the bottom, and $d_2$ is minimum distance between the first holder at the top and the second holder at the bottom. If the film did not reproducibly form the desired indent, the indent formation process was repeated and/or the film was realigned or replaced. The oscillation step was then repeated to test for flexural robustness of the film. For current bioreactor films, the standard value of $d_1$ was 3.6 cm and the standard value of $d_2$ was 2.6 cm.

Cycling: Once the oscillation stage was complete, the flex fatigue cycling program was run. The cycling program was computer controlled to generate a 1 Hz sinusoidal oscillation in holder separation between $d_1$ and $d_2$. The test was carried out continuously without pause or in blocks of 250 cycles separated by a 10 second pause. At the beginning of each program or block of cycles, a ramp step in the program moved the holders to a separation distance of $d_1$.

Testing: A dye penetration test was used to determine whether a perforation or breaking was formed in the film. The cycling was stopped and the film was moved using manual control to a clamp separation distance of $d_1$. A cotton swab was soaked in a solution of 1 weight percent dye in 50% ethanol/50% water (by volume) and wiped against the interior of the damaged area of the film, while a paper wipe was held against the outside of the film. If dye penetrated through the film onto the paper wipe, a perforation, breakage or leakage had been detected. After wiping with the dye-soaked cotton swab, a clean cotton swab was used to remove residue of the dye from the interior surface of the film. In the case that no perforation was detected, but some dye penetrated into delaminated layers of the interior surface, an interior break had been detected. Exterior surface breaks were detected visually without dye by the whitening or roughening of the film.

Example 2

Figure 6A:
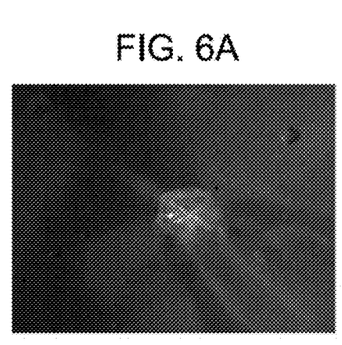
FIG. 6A shows whitening of a film that is part of a 50 L cell culture bag under rocking motion, tested in a rocker test as shown in FIG. 1.
Figure 6B:
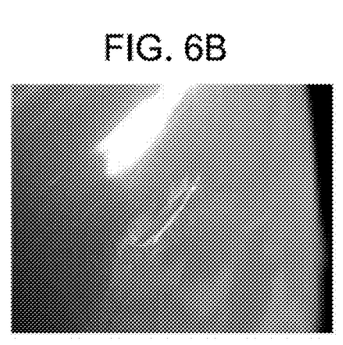
FIG. 6B shows delamination and/or crack formation on the same film as shown in FIG. 6A.
Figure 6C:
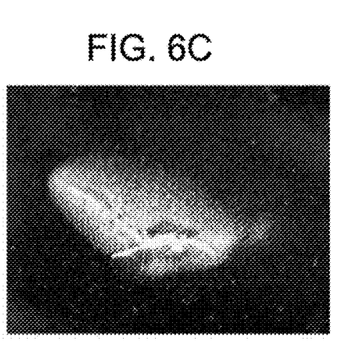
FIG. 6C shows breaking of the same film as shown in FIG. 6A.
Figure 7A:
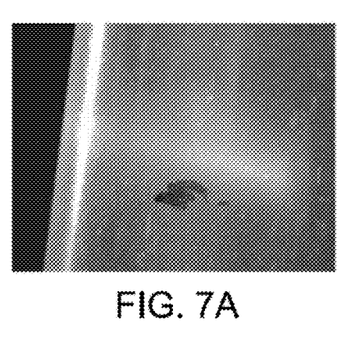
FIG. 7A shows whitening of a film mounted on a system as shown in FIG. 3 in a flexural fatigue test.
Figure 7B:
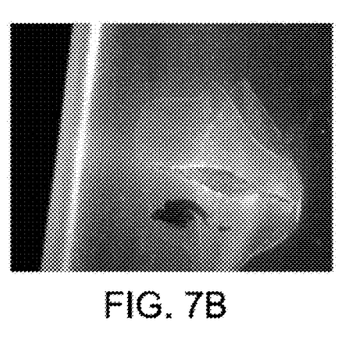
FIG. 7B shows delamination and/or crack formation on the film as shown in FIG. 7A.
Figure 7C:
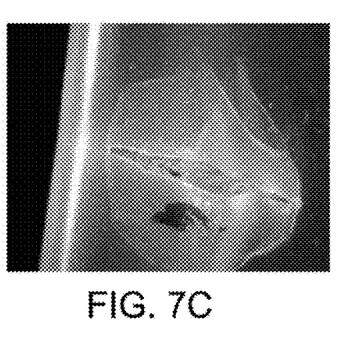
FIG. 7C shows breaking of the film as shown in FIG. 7A, in accordance with one embodiment of the invention.

Comparative Analysis of Progression of Failure Mode Using Present Method and a Rocker Test The progression of failure using the present method was compared to the progression of failure using the rocker test. An actual 50 L bioreactor bag filled with medium was rocked under extreme conditions (such as rocker speed of 25 rpm, angle of 9°) on a rocker platform for at least 30 days. FIGS. 6A, 6B and 6C showed the different stages of failure mode progression of the film of the cell culture bag in a rocker test. In the case of the present method, the film was subjected to flexural fatigue testing (as described above) and experienced the different stages of failure mode progression of a film, such as whitening of the film (FIG. 7A), delamination or crack formation on the film (FIG. 7B) and perforation on the film and/or breaking of the film (FIG. 7C). In the rocker test, medium-filled cell culture bags were subjected to continuous rocking on the bioreactor for more than 30 days to generate different steps of failure, as shown in FIGS. 6A, 6B and 6C. In contrast, the folded films achieved failure (perforation or breaking, FIG. 7C) through different stages using the present method, such as whitening (FIG. 7A) and delamination or cracking (FIG. 7 B) of the film in only 8-10 hours.

Example 3

Parallel Flexural Fatigue Failure Testing for Multiple Films

The present system was also used for testing multiple films simultaneously. FIG. 8 shows one embodiment of the system that allowed testing of four films simultaneously. In FIGS. 8, 50 and 52 were the fixed and movable holders of the system, respectively. In case of multiple-film testing, the films were aligned (FIG. 8) such that the folded edge of each of the films was lined up with the edges of the holders and also in the same horizontal plane where the other films were placed. Four individually folded films were attached to the holders present at the top row of the mounting device of the system (FIG. 8). Weights were attached to the films extending out below the small holders at the bottom of the film, while the holders were open. Once the film was in a position, the four small holders at the bottom of the film were fastened around the film and the weight was removed. An angle iron was pressed against the films while the film holders were moved slowly together to form an indent as described before.

A 90° metal angle-iron, with a radius of curvature of approximately 2 mm was used to indent the film. The angle iron was positioned at the midpoint of the 1.5" gap between the first holder (top) and the second holder (bottom) for each of the four sets, such that the long edge was perpendicular to the folded edge of the film. The indenter was placed on the folded film, such that a plane that was normal to the folded edge of the film would bisect the 90° angle of the angle-iron. The angle iron was mounted on a sliding stage so that it was able to move along that surface of the plane without changing the orientation of its 90° angle. To form the indented surface on the folded film, the angle iron was slid forward to contact the film. While the distance between the two holders was decreased by manual control, the angle iron was slid forward to remain in contact with the film. When the angle-iron touched the first holder or the second holder of the film, it was no longer in contact with film. At that point, the distance between the first holder at the top and the second holder at the bottom of the film was slowly increased to return to their original positions, and the angle iron was withdrawn to its original position, in continuous contact with the film. The indentation formation process was repeated for two more times, with the angle-iron sliding to stay in continuous contact with the film. The angle iron was removed and the distance between the two holders was optimized under computer control.

At this point, oscillating the holders to form a reproducible displacement on the film, cycling of the indentation and oscillation process, and recording of the failure mode were conducted as described earlier. A program of 0.1 Hz sinusoidal oscillation with holder separation between $d_1$ and $d_2$ for 30 cycles was run and monitored to verify that the indented deformation was successful. The indent formation process was repeated and/or the film was realigned or replaced to form the desired indent on the film. The oscillation cycle was also repeated to generate desired reproducible displacement on the indented film.

For specific commercial films, the standard value of $d_1$ is 3.66 cm and the standard value of $d_2$ is 2.64 cm. Once the indent formation was complete, the flexural fatigue cycling program was run. The cycling program was computer controlled to generate 1 Hz sinusoidal oscillation in holder separation between $d_1$ and $d_2$. The test may run continuously without pause or in blocks of 250 cycles separated by a 10 second pause. At the beginning of each program or block of cycles, a ramp step in the program moves the holders to a separation distance of $d_1$.

A dye penetration test was used to determine whether a perforation was formed in the film. The cycling was stopped and the film was moved using manual control to a holder separation distance of $d_1$. A cotton swab was soaked in a solution of 1 weight percent dye in 50% ethanol/50% water (by volume) and wiped against the interior of the damaged area of the film, while a paper wipe was held against the outside of the film. If some dye penetrated through the film onto the paper wipe, a perforation was detected. After wiping with the dye-soaked cotton swab, a clean cotton swab was used to remove residue of the dye from the interior surface of the film. In the case where no perforation was detected, but some dye penetrated into delaminated layers of the interior surface, an interior break was detected. Exterior surface breaks were detected visually without dye, by monitoring the whitening or roughening of the film.

Figure 9:
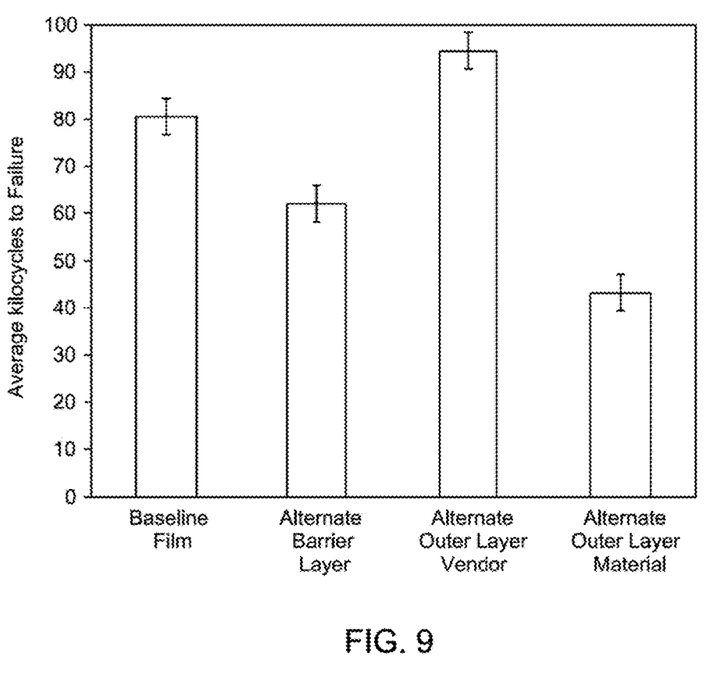
FIG. 9 is a graph showing the results of testing four different films using the system of FIG. 8, in accordance with one embodiment of the invention.

The bar graph of FIG. 9 shows the results from simultaneous testing of four different films using one embodiment of the system of FIG. 8. The "baseline film" as labeled in FIG. 9 was a multilayer film that performs well in an extended testing of 30 days on a rocking platform. The "alternate barrier film" as labeled in FIG. 9 had the same film structure with material variation in the oxygen barrier layer. The "alternate outer layer" was same as the baseline film except that a different grade of resin was used to form the outer layer. The "alternate outer layer material" was the same film as the baseline film, except the outer layer was made of polymer that was different from the other three multilayer films. The statistical data showed >95% confidence that each film is distinguishable from the others. Even films with minimal difference in material composition were distinguishable by the present method and system. Such minor differences are not detectable by the rocker test alone.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for testing flexural fatigue resistance of single-layer or multi-layer films, comprising:
   (a) introducing a fold into one or more than one film;
   (b) mounting the folded film such that one end of the folded film is held by a first film holder and the other end of the folded film is held by a second film holder, wherein the two film holders are positioned on an axis A1, the fold in the film is parallel to A1, the folded film has one axis A2 parallel to the fold and a second axis A3 perpendicular to the fold;
   (c) contacting the folded edge of the film with an indenter to create an indentation having a depth or a radius of curvature, or a combination thereof, on the mounted film;
   (d) oscillating at least one of the film holders to generate a reproducible displacement in the indented film of step (c); and
   (e) recording the flexural fatigue resistance of the indented film to the reproducible displacement.

2. The method of claim 1, wherein the reproducible displacement in the indented film is produced along the axis A1.

3. The method of claim 1, further comprising moving the indenter in a direction that is perpendicular to the axis A2 and parallel to the axis A3.

4. The method of claim 1, wherein the indentation is formed by contacting the mounted film with the indenter at an angle ranging from about 0° to about 90° from the axis A2.

5. The method of claim 1, wherein the indenter is an angle-iron comprising an angle ranging from about 10° to about 170°.

6. The method of claim 5, wherein the indenter has a radius of curvature ranging from about 0.1 mm to about 10 mm.

7. The method of claim 1, wherein the indenter is a rigid cylinder, elliptic cylinder, hemicylinder or hemi-elliptic cylinder having a diameter or long axis length ranging from about 0.5 mm to about 20 mm.

8. The method of claim 1, wherein the reproducible displacement comprises a cyclic displacement, a linear displacement, a sinusoidal displacement, or combinations thereof.

9. The method of claim 1, wherein the film is mounted in a substantially stretched form.

10. The method of claim 9, wherein the mounted film is further stretched by adding a load on the film.

11. The method of claim 1, wherein step (d) is repeated for 2 to 10 cycles to form the indentation.

12. The method of claim 1, wherein steps (d) and (e) are repeated for 1 to 5000000 cycles to measure flexural durability of the film.

13. The method of claim 1, wherein the depth of the indentation formed on the film ranges from about 5 mm to about 500 mm.

14. The method of claim 1, wherein at least one of the film holders is cycled along the axis A1 in a sinusoidal wave form with a frequency ranging from about 0.01 Hz to about 100 Hz and a displacement ranging from about 10 mm to about 100 mm.

15. The method of claim 1, further comprising oscillating both the film holders to generate the reproducible displacement.

16. The method of claim 1, wherein step (d) is performed until a failure of the film occurs, wherein the failure of the film comprises whitening of the film, cracking of the film, delamination of the film, perforation of the film, or combinations thereof.

* * * * *